United States Patent [19]

Degnan et al.

[11] Patent Number: 5,015,360
[45] Date of Patent: May 14, 1991

[54] PRODUCTION OF HYDROCARBON FRACTIONS BY HYDROCRACKING

[75] Inventors: Thomas F. Degnan, Moorestown; Garry W. Kirker, Washington Township, Gloucester County, both of N.J.; Richard F. Socha, Newtown, Pa.; Michael R. Stapleton, Freehold; Ivy D. Johnson, Medford, both of N.J.

[73] Assignee: Mobil Oil Corporation, Fairfax, Va.

[21] Appl. No.: 459,216

[22] Filed: Dec. 29, 1989

Related U.S. Application Data

[63] Continuation-in-part of Ser. No. 879,787, Jun. 27, 1986, Pat. No. 4,859,648, which is a continuation-in-part of Ser. No. 687,414, Dec. 28, 1984, abandoned.

[51] Int. Cl.$^5$ ............................................. C10G 47/12
[52] U.S. Cl. .................................... 208/110; 208/109; 208/112; 502/84

[58] Field of Search ............... 208/109, 110, 112, 118, 208/119, 120, 121, 144; 502/84

[56] References Cited

U.S. PATENT DOCUMENTS

| | | | |
|---|---|---|---|
| 4,579,832 | 4/1986 | Shabtai et al. | 502/84 |
| 4,637,991 | 1/1987 | Battiste et al. | 502/84 |
| 4,637,992 | 1/1987 | Lewis et al. | 502/84 |
| 4,812,222 | 3/1989 | Kirker et al. | 208/110 |

*Primary Examiner*—Anthony McFarlane
*Assistant Examiner*—Nhat Phan
*Attorney, Agent, or Firm*—Alexander J. McKillop; Charles J. Speciale; Edward F. Kenehan, Jr.

[57] ABSTRACT

A process for hydrocracking 343° C.+ feedstock is disclosed. The process employs a catalyst which comprises a layered silicate, such as magadiite or kenyaite, which contains interspathic polymeric silica. The catalyst also contains at least one base metal, i.e., Cr, Mo, W, Fe, Co, and Ni.

14 Claims, 3 Drawing Sheets

PRODUCTION OF HYDROCARBON FRACTIONS BY HYDROCRACKING

CROSS-REFERENCE TO RELATED APPLICATIONS

This application is a continuation-in-part of copending U.S. patent application Ser. No. 879,787, filed Jun. 27, 1986, now U.S. Pat. No. 4,859,648, which is a continuation in part of U.S. patent application Ser. No. 687,414, filed Dec. 28, 1984, now abandoned. The entire contents of the above-mentioned application in this Cross-Reference section are expressly incorporated herein by this reference.

BACKGROUND

This application is directed to the production of high quality hydrocarbon fractions by hydrocracking high boiling hydrocarbons.

One of the most valuable products of the refining of crude mineral oils is lubricating oil. Common practice is to recover lubricating oil components by extracting undesirable components, such as sulfur compounds, oxygenated compounds, and aromatics, from a straight run distillate fraction with a selective solvent. However, with the gradual decline in the availability of paraffinic base crudes and a corresponding increase in the proportion of naphthenic and mixed naphthenic and asphaltic base crudes, it is becoming increasingly difficult to recover sufficient quantities of components suitable for lubricating oils by extraction.

One method which has been suggested as a remedy of this situation is hydrogenation of high boiling hydrocarbon charge stocks which do not contain a substantial quantity of lube oil components in order to produce such components. An example of this method is represented in U.S. Pat. No. 3,142,635, incorporated herein by reference, teaching the production of very high viscosity index oils in high yields of a unique kind of using a special catalyst. This method teaches the use of hydrocracking catalysts such as platinum on silica-alumina as well as others taught in U.S. Pat. No. 2,945,806, incorporated herein by reference. The use of such catalysts results in a product of high viscosity index. However, it is recognized that substantial amounts of undesirable low viscosity index polycyclic aromatics which are oxidatively unstable will remain in the lube oil produced by hydrocracking unless removed by distillation. Another way of dealing with such impurities is taught in U.S. Pat. No. 3,530,061, incorporated herein by reference, which employs hydroprocessing the hydrocracked product with a hydrogenation-dehydrogenation catalyst comprising a support material of low cracking activity, e.g., platinum on alumina at temperatures and pressures which limit conversion to 600° F.- products. However, this procedure suffers from the drawback of requiring an additional hydroprocessing step. In U.S. Pat. No. 4,176,090, catalysts which comprise layered clays (smectites) intercalated with inorganic metal polymers, e.g., aluminum chlorhydrol, which form polymeric cationic hydroxy metal complexes are disclosed as suitable for conventional petroleum conversion processes such as catalytic cracking, hydrocracking, hydrotreating, and isomerization. U.S. Pat. No. 4,579,832 discloses the use of layered smectite clays, e.g., montmorillonite, which are cross-linked with hydroxy-Al oligomers, as hydrocracking catalysts.

SUMMARY

In accordance with an aspect of this application, there is provided a process comprising hydrocracking a hydrocarbon feedstock having an initial boiling point above 343° C. in the presence of a catalyst having cracking and hydrogenating activity, said catalyst comprising a layered silicate containing interspathic polymeric silica, in order to produce a hydrocarbon product having at least 35 percent by weight of hydrocarbons having a boiling point below 343° C., said catalyst further comprising at least one metal selected from the group consisting of Cr, Mo, W, Fe, Co, and Ni.

According to another aspect of this application, there is provided a process comprising hydrocracking a hydrocarbon feedstock having an initial boiling point above 343° C., said hydrocarbon comprising waxy components, said hydrocracking taking place in the presence of a catalyst having cracking and hydrogenating activity, said catalyst comprising magadiite containing interspathic polymeric silica and interspathic polymeric alumina, said catalyst further comprising Ni and W, said hydrocracking taking place under conditions to produce a hydrocarbon product having at least 50 percent by weight of hydrocarbons having a boiling point below 343° C., whereby the content of the waxy components of the feedstock are reduced, e.g., as evidenced by a reduction in pour point of the 343° C.+ fraction.

According to another aspect of this application, there is provided a process comprising hydrocracking a hydrocarbon feedstock having an initial boiling point above 343° C., said hydrocracking taking place in the presence of a catalyst having cracking and hydrogenating activity, said catalyst comprising kenyaite containing interspathic polymeric silica and interspathic polymeric alumina, said catalyst further comprising Ni and W, said hydrocracking taking place under conditions to produce a hydrocarbon product having at least 70 percent by weight of hydrocarbons having a boiling point below 343° C., and at least 30 percent by weight of hydrocarbons having a boiling point between 165° and 343° C.

EMBODIMENTS

The present hydrocarbon feedstock may have a boiling point above about 343° C. (650° F.) and may contain polycyclic aromatics. To the extent that the product contains polycyclic aromatics, the product is improved in that it contains a lesser proportion of polycyclic aromatic hydrocarbons than the charge stock which enhances the oxidation stability and viscosity index of the product.

The hydrocracking process can be carried out at temperatures ranging from about 250° C. to about 500° C., e.g., from about 300° C. to about 450° C.; hydrogen pressures ranging from about 2 to 21 MPa, e.g., from about 3 to 21 MPa; liquid hourly space velocities ranging from about 0.05 to about 10, e.g., from about 0.2 to 3; $H_2$ circulations ranging from about 50 or 500 to about 10,000 scfb, e.g., from about 2000 to about 6000 scfbl and conversions to 650° F.− (343° C.−) product of greater than about 50 percent volume of charge.

The hydrocarbon feed material suitable for use in the present invention can be substantially any hydrocarbon feed material having an initial boiling point above about 316° or 343° C. (600° F. or 650° F.). Such materials include heavy gas oils, residual stocks, cycle stocks, topped crudes, reduced crudes, and relatively high boiling point hydrocarbon fractions of cracking derived from coal, tars, pitches, asphalts and shale oils. These materials can be obtained by fractionation, as by vacuum distillation, of crude oils identified by their source, e.g., Pennsylvania, Mid-Continent, Gulf Coast, West Texas, Amal, Kuwait, Barco and Statfjord. Feed material obtained from resids should be made substantially free of asphaltenes prior to hydrocracking.

The hydrocarbon feedstock may be treated in order to reduce or substantially eliminate heteroatom content prior to the hydrocracking step. As necessary, the feedstock may be hydrotreated under mild or moderate hydroprocessing conditions to reduce sulfur, nitrogen, oxygen, and metal content in the feedstock. Generally, a hydrocarbon feedstock used in hydrocracking should have a low metals content, e.g., less than about 200 ppm, in order to avoid obstruction of the catalyst and plugging of the catalyst bed. The mild to moderate hydrotreating conditions employed include pressures 2 to 21 MPa and $H_2$ consumptions of 20 to 280 $m^3/m^3$. Conventional hydrotreating process conditions and catalysts may be employed, e.g., those set out in U.S. Pat. No. 4,283,272 to Garwood et al, incorporated herein by reference. A method for hydrotreating resids which contain naphthenes and which employs polymeric metal oxide intercalated layered oxides is set out in U.S. Pat. No. 4,600,503, incorporated herein by reference.

When hydrocracked, the high boiling hydrocarbon feed material employed in the present process undergoes conversion of some high molecular weight compounds to lower boiling materials, some of which are unsuitable for use as lube oils, but are quite suitable for use as gasolines or distillates. A fraction of the polycyclic aromatic and naphthenic compounds present in the feedstock is hydrogenated and cracked to form lower molecular weight naphthenes and paraffins. Because the polycyclics tend to degrade the viscosity index and stability of the stock, conversion of these materials is desirable, particularly in view of the tendency for paraffins thus made to be isomerized during hydrocracking. Ring opening of polycyclic compounds and isomerization of paraffins reduces the pour point of the hydrocracked products and improves the VI. Because these transformations are accomplished by the catalysts of this invention, the lube products obtained have low pour points and high VI.

The feedstocks suitable for use herein may contain waxy components. As part of the present hydrocracking process, paraffinic components of the initial feedstock undergo isomerization to iso-paraffins with some cracking to lower molecular weight materials. The waxy components (straight chain and slightly branched chained paraffins) are at least partially removed from the high boiling fraction so that its pour point (ASTM D-97) is decreased. The present process is of particular utility with highly paraffinic feeds because, with feeds of this kind, the greatest improvement in pour point may be obtained.

The feedstock may contain relatively large proportions of waxy hydrocarbons in the 345° C.+ (about 650° F.+) fraction; these waxy hydrocarbons may be characterized chemically as straight chain and slightly branched chain paraffins, i.e., n-paraffins and iso-paraffins having short chain branches. The higher molecular weight paraffins will generally be slightly branched chain materials as opposed to being wholly straight chain but because the branchings are relatively short, the linear chain characteristics will predominate, so that the material will be of a waxy nature, contributing to a high pour point.

In those cases where a lower pour point lube is desired, the lube oil hydrocrackate fraction can be further dewaxed by any suitable means, such as solvent dewaxing and catalytic dewaxing. Catalytic dewaxing of lube stocks is described in Reissue Patent No. 28,398 to Chen et al as well as in U.S. Pat. Nos. 3,755,138, 4,176,050, and 4,283,272, all of which are incorporated herein by reference.

The catalyst employed in the hydrocracking process of the present invention is particularly suited to preparing lubes by hydrocracking high boiling hydrocarbon feeds which contain polycyclic aromatics or naphthenes. These catalysts by their inherent structure provide access of polycyclic materials to the dual functional metal-acid components present in the catalyst thereby facilitating conversion to more advantageous materials.

Many layered materials are known which have three-dimensional structures which exhibit their strongest chemical bonding in only two dimensions. In such materials, the stronger chemical bonds are formed in two-dimensional planes and a three-dimensional solid is formed by stacking such planes on top of each other. However, the interactions between the plans are weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van der Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules.

Laminated materials such as clays may be modified to increase their surface area. In particular, the distance between the interlamellar layers can be increased substantially by absorption of various swelling agents such as water, ethlene glycol, amines, ketones, etc., which enter the interlamellar space and push the layers apart. However, the interlamellar spaces of such layered materials tend to collapse when the molecules occupying the space are removed by, for example, exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing." These values indicate the distance between, for example, the uppermost margin of one layer with the uppermost margin of its adjoining layer. If the layer thickness is known, the interlayer spacing can be determined by subtracting the layer thickness from the basal spacing.

The hydrocracking catalyst employed in the present invention comprises a layered silicate containing interspathic polymeric silica. The interlayer distance of the silicate is such that polycyclic hydrocarbon components of the feed can pass between adjacent layers of the silicate, preferably a distance greater than about 10 angstroms or even 15 angstroms, say about 15 to 20 angstroms. The catalyst possesses hydrogenation and cracking activity, the latter of which may be enhanced by the presence of an interspathic polymeric oxide comprising an element selected from the group consisting of Al, B, Cr, Ga, In, Mo, Nb, Ni, Ti, Tl, W, and Zr, e.g., polymeric alumina. Hydrogenation activity can be provided by incorporating any suitable hydrogenation component into the catalyst, e.g., an element selected from the group consisting of Ru, Rh, Pd, Os, Ir, and Pt, e.g., palladium. These noble metals are particularly suited to applications where feeds to the hydrocracking stage are low in sulfur. In those instances where raw untreated feeds are to be processed, it would be more appropriate to use base metal hydrogenating components, particularly combinations of metals form Groups VI A (Cr, Mo, and W) and VIII A (Fe, Co, Ni, Ru, Rh, Pd, Os, Ir, and Pt) of the Periodic Table. The catalysts employed in the present process contain one or more base metals, i.e., Cr, Mo, W, Fe, Co, and Ni. The base metals are the above-mentioned Group VIA and VIIIA metals, less the noble metals, Ru, Rh, Pd, Os, Ir, and Pt.

The process of the present invention utilizes a hydrocracking catalyst which comprises a layered silicate which contains interspathic polymeric silica. The layered silicate may also comprise an interspathic polymeric oxide of an element selected from the group consisting of Al, B, Cr, Ga, In, Mo, Nb, Ni, Ti, Tl, W, and Zr, e.g., polymeric silica-alumina between the layers of the silicate material. Preferably, such "pillared" materials are thermally stable, i.e., capable of withstanding calcining at a temperature of about 450° C. for at least 2 hours without significant reduction, (e.g., not greater than 10 or 20%), in the spacing between the silicate layers. Preferably, such materials can withstand prolonged exposure to the conditions encountered during hydrocracking. Polymeric interspathic silicas displaced between silicate layers are considered to include oxides of two or more repeating units, preferably three or more repeating units, e.g., four or more or even five or more repeating units. The extent of polymerization of the interspathic polymeric silica is believed to affect the ultimate interlayer separation of the layered product; that is to say, the greater the extent of polymerization occuring, the greater the interlayer distance resulting in the pillared layered silicate. A layered material suited for use in the present hydrocracking process, having a desired interlayer spacing can be prepared according to the method set out in U.S. patent application Ser. No. 897,787, filed Jun. 27, 1986, incorporated herein by reference. In this method, the interlayer spacing of the layered material can be tailored by careful selection of the "propping" agent used to separate the layers during treatment with interspathic polymeric silica precursors which are eventually converted to the thermally stable polymeric silica "pillars." Indeed, a wide range of interlayer spacings can be achieved by this method. Interlayer distances can range anywhere from 2 to 30 angstroms or more, e.g., greater than 5, 10, 15, or 20 angstroms, depending largely on the type of "propping" agent used as well as the layered chalcogenide being treated. For the purpose of the present invention, interlayer distances which result in interlayer spacings large enough to accommodate polycyclic aromatics are desirable, e.g., interlayer spacings greater than 8 angstroms or preferably greater than 10 angstroms, e.g., about 10 to 20 angstroms.

The pillared layered silicates employed herein can be prepared by treating a layered silicate which contains ion exhange sites having interspathic cations associated therewith, with an organic compound which is a cationic species or capable of forming a cationic species to effect exchange with the interspathic cations. An electrically neutral compound capable of conversion to the interspathic polymeric metal or non-metal oxide is provided between the layers of the treated layered silicate. The compound is then converted to the interspathic polymeric silica to form the layered material.

The pillared layered silicate employed in the present invention can be prepared by treating a layered silicate, e.g., a high silia alkali silicate such as synthetic magadiite, or synthetic kenyaite. These pillared layered silicate materials possess a framework composed essentially of only tetrahedral sheets, i.e., silicon is coordinated with four oxygen atoms, condensed on each other. These materials lack octahedtral sheets, such as those found in clays, wherein an element such as aluminum is coordinated with six oxygen atoms. Besides interspathic polymeric silica, interspathic polymeric oxides of one or more elements selected from the group consisting of B, Al, Ga, In, and Tl can also be incorporated between the layers of the silicate either separate from or incorporated into the interspathic polymeric silica pillars. Interspathic polymeric alumina is particularly useful in imparting acidic activity to the layered silicate. Interspathic polymeric oxides containing silica-alumina are a preferred pillar for these layered silicates.

Pillared silicates containing from about 5 to 50 wt % silica-alumina incorporated as the pillar material are desirable. Particularly preferred are silicates containing from about 10 to 20 wt % silica-alumina as the pillared material. The silica/alumina molar ratio ($SiO_2/Al_2O_3$) of the pillared material may vary between about 5 to 1000 or even greater.

Layered silicate materials of relatively high interplanar distance (d-spacing), e.g., greater than about 10, 15, 18, 20, 25, or even 30 or more angstroms, can be prepared using the above-discussed techniques. These materials are capable of being exposed to severe conditions such as those encountered in calcining, e.g., at temperatures of about 450° C. for about two or more hours, e.g., four hours, in nitrogen or air, without significant decrease, perhaps, e.g., less than about 10%, in interlayer distance. The size of interspathic polymeric silica contained within the final product can be greatly varied because the polymeric silica precursor species are introduced in an electrically neutral form such that the amount of interspathic material incorporated within the layered silicate is not dependent upon the charge density of the original layered silicate starting material. Charge density should be taken into consideration in determining the suitability of the cationic species introduced between the layers in the procedure used to prop open the layers prior to pillaring. The use of an electrically neutral polymeric oxide precursor allows the formation of materials in which the interlayer spacing can be widely varied.

The layered silicate starting material can contain ion exchange sites having interspathic cations associated therewith. Such interspathic cations may include hydrogen ion, hydronium ion, or alkali metal cation. The starting material is treated with a "propping" agent comprising a source of organic cation, which source may include the cation itself, in order to effect an exchange of the interspathic cations resulting in the layers of the starting material being propped apart. In particular, alkylammonium cations have been found useful. Thus $C_3$ and large alkylammonium cations, e.g., n-octylammonium, can be readily incorporated within the interlayer species of the layered silicates, serving to prop open the layers in such a way as to allow incorporation of the polymeric chalcogenide precursor. The extent of the interlayer spacing can be controlled by the size of the organoammonium ion employed to that use of the n-octylammonium cation can achieve a d-spacing of about 2 to 5 A or an opening of about 2–3A, whereas to achieve an interlayer opening of 10 to 20A, an n-octylammonium cation or a cation of equivalent length is required. The organic ammonium cations separating the silicate layers may also be formed in situ by reaction of the neutral amine species with interlayer hydrogen or hydronium cations of the layered silicate starting material.

The polymeric oxide pillars are formed from a precursor material which is preferably introduced between the layers of the organic "propped" species as a cationic, or more preferably, electrically neutral, hydrolyzable compound of the desired elements. The precursor material is preferably an organic compound containing said desired elements which is a liquid under ambient conditions. In particular, hydrolyzable compounds, e.g., alkoxides, of the desired elements of the pillars are utilized as the precursors. Suitable polymeric silica precuror materials include tetraalkylsilcates, e.g., tetrapropylorthosilicate, tetramethylorthosilicate, and, most preferably, tetraethylorthosilicate. Introduction of interspathic polymeric oxide of an element selected from the group consisting of Al, B, Cr, Ga, In, Mo, Nb, Ni, Ti, Tl, W, and Zr to the pillar system can be achieved by contacting a hydrolyzable compound of the desired element with the organic "propped" species before, after or simultaneously with the contacting of the layered chalcogenide with the silicon compound. The hydrolyzable aluminum compound employed may be an aluminum alkoxide, e.g., aluminum isopropoxide.

After hydrolysis to produce the polymeric oxide pillars and calcination to remove the organic propping agent, the final pillared product may contain residual exchangeable cations. Such residual cations in the layered material can be ion exchanged by known methods with other cationic species to provide or alter the catalytic activity of the pillared product. In particular, hydrogenation components containing at least one element selected from the group consisting of Cr, Mo, W, Fe, Co, and Ni, preferably W and Ni, can be introduced by ion-exchange of impregnation techniques known in the art. Representative ion exchange techniques are disclosed in a wide variety of patents including U.S. Pat. Nos. 3,140,249; 3,140,251; and 3,140,253, all of which are incorporated herein by reference. Generally, the hydrocracking catalyst of the present invention can contain about 0.1 to 20 wt %, preferably about 0.5 to 15 wt % hydrogenation component.

The polymeric oxide precursor-containing product can be exposed to suitable conversion conditions, such as hydrolysis and/or calcination to form the layered material employed in the present invention. The hydrolysis step may be carried out by any method, for example, by interspathic water already present in the organic-"propped" layered silicate material. Because of the effect of interspathic water on hydrolysis, the extent of hydrolysis may be modified by varying the extent to which the organic-"propped" species is dried prior to addition of the polymeric oxide precursor. As noted earlier, the product after conversion to the polymeric oxide form may be exposed to conditions which remove organic compounds such as the organic cation propping agents, e.g., exposure to elevated temperatures such as those encountered by calcining in air or nitrogen. Such products, especially when calcined, exhibit high surface area, e.g., greater than 200, 300, 400 or even 600 $m^2/g$, and thermal and hydrothermal stability.

The pillared silicates can be composited with porous inorganic oxide matrix materials such as silica-alumina, silica-magnesia, silica-zirconia, silica-thoria, silica-beryllia, and silica-titania, as well as ternary compositions, such as silica-alumina-thoria, silica-alumina-zirconia, silica-alumina magnesia, and silica-magnesia-zirconia. The matrix may be in the form of a cogel. The relative proportions of pillared silicate component and inorganic matrix, on an anhydrous basis, may vary widely with the silicate content ranging from about 1 to about 99 percent by weight and more usually in the range of from about 5 to about 80 percent by weight of the dry composite.

Layered silicates, e.g., high silica alkali silicates such as magadiite, natrosilite, kenyaite, makatite, nekoite, kanemite, okenite, dehayelite, macdonaldite, and rhodesite, unlike swellable clays, lack octahedral sheets, i.e., sheets composed of atoms which are octahedrally coordinated with oxygen atoms. Such high silica alkali silicates, as well as their synthetic analogues are well-suited as starting materials used in preparing the pillared layered silicates employed in the process of the present invention. Without stable intercalated pillars, these starting materials tend to undergo collapse of their layers at elevated temperatures, which results in low porosity and low surface area.

The layered silicate starting materials known as high silica alkali silicates, whose layers lack octahedral sheets, can be prepared hydrothermally from an aqueous reaction mixture containing silica and caustic at relatively moderate temperatures and pressures. These layered silicates may contain tetracoordinate framework atoms other than Si. Such layered silicates can be prepared by co-crystallizing in the presence of non-silicon tetravalent elements, e.g., those selected from the group consisting of B, Al, Ga, In, and Tl as well as any other such elements which are catalytically useful when incorporated in the silicate structure.

Alternatively, non-silicon framework elements already in a layered silicate may be substituted by a tetracoordinate element. Both co-crystallized and substituted layered high silica alkali silicates may be treated by the procedure described above to provide layered materials containing interspathic polymeric oxide pillars.

Synthetic magadiite materials which contain interspathic polymeric oxides are particularly suited to use in the hydrocracking process of the present invention. Synthetic magadiite is readily synthesized hydrothermally from a reaction mixture containing inexpensive sources of silica and caustic. Tetracoordinate elements other than silicon, e.g., those selected from the group consisting of B, Al, Ga, In, Tl and other catalytically useful metals, may be added to the reaction mixture to produce synthetic magadiite layered silicates. Preferably, such elements are selected from the group consisting of Al and Ga. An organic directing agent may also be added to the reaction mixture. The reaction mixture for synthetic layered silicate materials can be described in molar ratios as follows:

| | |
|---|---|
| $SiO_2/X_2O_3 =$ | 10 to infinity where X can be B, Al, Ga, In and/or Tl or other catalytically useful metal |
| $M^+OH^-/SiO_2 =$ | 0 to 0.6 (preferably 0.1–0.6) M = an alkali metal |
| $H_2O/SiO_2 =$ | 8–500 |
| $R/SiO_2 =$ | 0–0.4 | where R can be an organic such as benzylriethylammonium chloride, benzyltrimethylammonium chloride, dibenzyldimethylammonium chloride, N, $N^1$-dimethylpiperazine, triethylamine, or other quaternary compounds or heterocyclic amines.

The reaction mixture can be maintained at a temperature of about 100° to 200° C. for anywhere from about 1 to 150 days in order to form a product having the following composition:

| | |
|---|---|
| % N = | 0 to 3, e.g., 0 to 0.3 |
| $SiI_2/X_2O_3 =$ | 10 to infinity where X may be in the tetrahedtral or octahedtral position |
| $M_2O/SiO_2 =$ | 0 to 0.5, e.g., 0.05 to 0.1 |

The synthetic layered silicate materials thus prepared have a low surface area. Introduction of interspathic polymeric oxides according to the above-described procedure can increase the surface area of these materials. Generally, the synthetic magadiite (or layered silicate) material is acidified by any suitable means, e.g., treatment with aqueous 0.1N HCl, and thereafter treated with a "propping" agent. A suitable compound capable of conversion to a polymeric oxide is combined with the "propped" layered silicate and the resulting material can then be calcined to remove residual organics.

EXAMPLE 1

Silica-alumina pillared magadiite was prepared as follows. Synthetic magadiite was used in the as-synthesized sodium form. Twelve (12) parts (dry basis) of the synthetic magadiite were reacted with 26 parts octylamine in 66 parts distilled water for 24 hrs at ambient temperature. The reactant product was treated with a flocculating agent and filtered. The resulting dry product was treated with a solution of 1 part aluminum isopropoxide in 40 parts tetraethylorthosilicate which had been prereacted at 100° C. for 16 hrs and 3 days at ambient temperature; the treatment with this mixture was carried out for 48 hours at ambient temperature. The reactant product was filtered, air dried, then dried in vacuuo at about 90° C. overnight. Finally, the dried product was heated at 5° F./min in $N_2$ (3 v/v/min) to 1000° F., held 2 hours, air flow was slowly increased and reduced $N_2$ and held 2 more hours in air (3 v/v/min) to 1000° F.

The silica-alumina pillared magadiite had the characteristics set forth in Table 1.

TABLE 1

| Properties of Silica-Alumina Pillared Magadiite | |
|---|---|
| $SiO_2$, wt % | 95.1 |
| $Al_2O_3$ | 2.0 |
| N | 0.03 |
| Ash | 98.3 |
| Surface Area, $m^2/g$ | 593 |
| Sorption | |
| $H_2O$, g/100 g | 21.5 |
| Cyclohexane | 15.9 |
| Alpha (1000° F.) | 5 |

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the highly active silica-alumina cracking catalyst taken as an Alpha Value of 1 (Rate Constant = 0.016 sec$^{-1}$). The Alpha Test is described in U.S. Pat. No. 3,354,078 and in the *Journal of Catalysis*, Vol. 4, p. 527 (1967); Vol. 6, p. 278 (1966); and Vol. 61, p. 395 (1980), each incorporated herein by reference as to that description. The experimental conditions of the Alpha Test preferably include a constant temperature of 538° C. and a variable flow rate as described in detail in the *Journal of Catalysis*, Vol. 61, p. 395.

EXAMPLE 2

A 4 wt % of Ni/10 wt % W on silica-alumina pillared magadiite was prepared from the pillared magadiite of Example 1 by incipient wetness impregnation of ammonium metatungstate, drying at 120° C. overnight, calcination in air at 1° C./min to 538° C. for three hours, cooling the catalyst to room temperature, incipient wetness impregnation of the catalyst with $Ni(NO_3)_2$, drying at 120° C. overnight, and calcination in air a second time at 1° C./min to 538° C. for three hours.

EXAMPLE 3

The catalyst of Example 2 was charged to a reactor, presulfided, and used to convert a Statfjord distallate, with the properties shown in Table 2, at 1380 psig, 0.58 LHSV. Table 3 compares the results of this run with those obtained by hydrocracking over a conventional NiW Ultrastable Y catalyst under comparable conditions. The metals loadings of both the magadiite catalyst and Ultrastable Y catalyst were equivalent. This comparison shows that at approximately equivalent conversions, the product from the magadiite catalyst has a significantly lower pour point than that obtained from the Ultrastable Y catalyst.

TABLE 2

| Properties of Statfjord Distillate | |
|---|---|
| Viscosity (SUS) | 150 |
| Distillation (D2887) | |
| 1% | 653 |
| 5% | 696 |
| 50% | 784 |
| 95% | 877 |
| 99% | 915 |
| Hydrogen, % | 13.40 |
| Nitrogen, ppm | 620 |
| Sulfur, % | 0.43 |
| Paraffins | 30.7 |
| Mononaphthenes | 16.9 |
| Polynaphthenes | 17.7 |
| Aromatics | 34.7 |

TABLE 2-continued

| Properties of Statfjord Distillate | |
|---|---|
| KV 40° C., cs | 26.45 |
| KV 100° C., cs | 4.805 |
| Pour Point, °F. | 95 |
| Cloud Pt., °F. | 112 |
| Flash, COC, °C. | 421 |

TABLE 3

Comparison Between Magadiite and USY Catalysts Of Hydrocracking of Statfjord Distillate

| Catalyst | NiW-Magadiite | NiW-USY |
|---|---|---|
| Temperature, °F. | 784 | 743 |
| Pressure, psig | 1380 | 1410 |
| LHSV | 0.58 | 1.0 |
| Conversion, % | 81 | 78 |
| Yields, wt % | | |
| 650° F.+ | 19 | 22 |
| 330–650° F. | 27 | 31 |
| $C_5$–330° F. | 33 | 41 |
| $C_1$–$C_4$ Gas | 21 | 6 |
| Pour Point of 650° F.+ Fraction, °F. | 45 | 75 |

EXAMPLE 4

A silica-alumina pillared kenyaite was prepared as follows. A sample of synthetic kenyaite was prepared in a manner similar to that reported by K. Beneke and G. Lagaly in *American Mineralogist*, Vol. 68, p. 818 (1983), incorporated herein by reference. A mixture of 10.22 g 87.2% KOH and 57.4 g of amorphous precipitated silica (HiSil 233) in 300 g water was crystallized in a 600 ml autoclave with stirring at 150° C. for 3 days. The product was filtered, washed with 4 liters water, and dried at 250° F. for one hour. The dried product had the following composition:

| 4.0% | K |
|---|---|
| 0.39% | $Al_2O_3$ |
| 68.0% | $SiO_2$ |
| 73.55% | Ash |

A sample calcined in air for one hours at 1000° F. had low surface area.

The synthetic K+-form kenyaite was intercalated with cetyltrimethylammonium bromide to swell the layers apart. To do this the as-synthesized kenyaite was added directly to a 1M cetyltrimethylammonium bromide solution, stirred for at least 2 hours, filtered and washed with $H_2O$. After the swollen kenyaite had air-dried to a powder, it was impregnated 1 g/1 g with tetraethylorthosilicate and thoroughly mixed by tumbling the closed polypropylene jar on a roller overnight. The impregnated material (200 g) was suspended in an aqueous solution of Al $(NO_3)_3$ (1000 g, 0.5M), stirred for 18 hours, filtered, air-dried, and then calcined in air for six hours at 540° C.

The finished material had the following properties:

| Surface Area, $m^2$/g | 582 |
|---|---|
| Ash, 1000° C., wt % | 90.58 |
| $SiO_2$, wt % | 85.3 |
| $Al_2O_3$, wt % | 2.9 |
| K, ppm | 305 |

EXAMPLE 5

A ten gram sample of the material from Example 4 was charged to a polypropylene bottle. Ten milliliters of an ammonium metatungstate (AMT, $(NH_4)_6W_{12}O_{39}\cdot 9H_2O$) solution (1.63 g/10 cc) was added slowly, over a 5-minute period, to the powdered kenyaite sample using a pipette to impregnate the material. The bottle was agitated frequently to guarantee a uniform distribution of the AMT. The impregnated material was dried at room temperature overnight and then at 110° C. for 24 hours. The dried material was then calcined in air by heating to 538° C. at a rate of 1° C./min and holding at the final temperature for three hours.

The calcined sample was then cooled to room temperature and impregnated with a nickel nitrate solution by again charging the material to a polypropylene bottle and dropwise slowly adding 10 ml of a $Ni(NO_3)_2\cdot 6H_2O$ solution (2.3 g Ni $(NO_3)_2\cdot 6H_2O/10$ cc). This material was dried in air at room temperature, and then in air at 110° C. for 24 hours. The final step involved calcining the material in air by heating to 538° C. at a rate of 1° C./min and holding at 538° C. for three hours.

EXAMPLE 6

Figure 1:
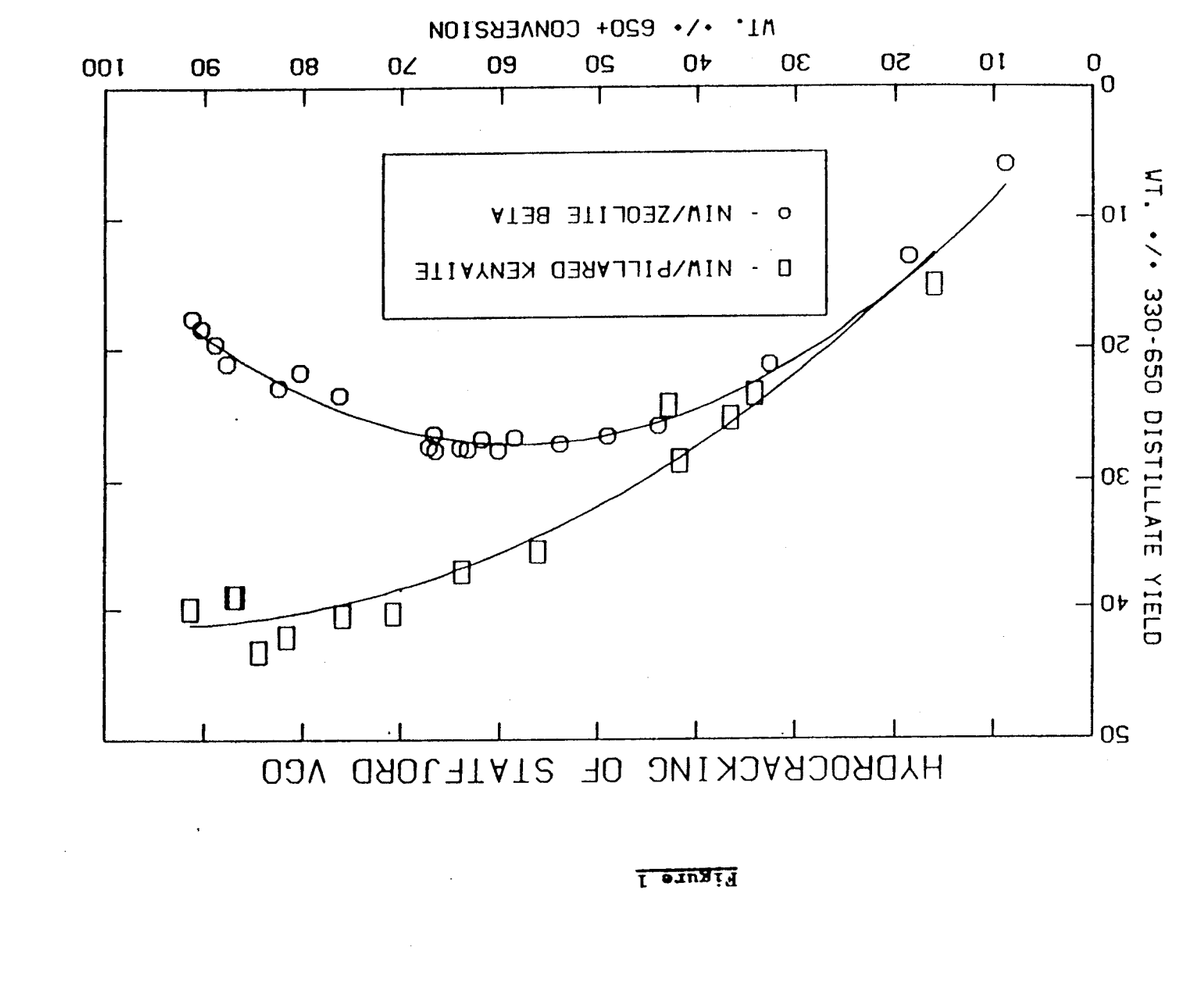
FIG. 1 compares the selectivity of a NiW/pillared kenyaite with an analogous NiW/zeolite beta catalyst for the conversion to 330°-650° F. distillate.

A 5.2 gram (11 cc) sample of the catalyst from Example 5 was charged to a reactor and used to hydrocrack a Statfjord vacuum gas oil at 1450 psig, 720° to 800° F., and 0.4 WHSV. The properties of the Statfjord vacuum gas oil are given in Table 2. FIG. 1 compares the selectivity of the NiW/pillared kenyaite with an analogous NiW/zeolite beta catalyst for the conversion to 330°–650° F. distillate. For this comparison, the NiW/zeolite beta catalyst was run under very similar conditions. These data show that the pillared kenyaite catalyst is capable of producing a higher yield of distillate than the NiW/zeolite beta catalyst. For example, at 80 wt % conversion to 650° F.−, the NiW/pillared kenyaite catalyst produced 17 wt % more distillate than the zeolite beta based hydrocracking catalyst. This result is significant, in view of the advantages of using a NiW/zeolite beta catalyst over other catalysts for maximum distillate yield as disclosed in U.S. Pat. No. 4,612,108, the entire disclosure of which is expressly incorporated herein by reference.

Figure 2:
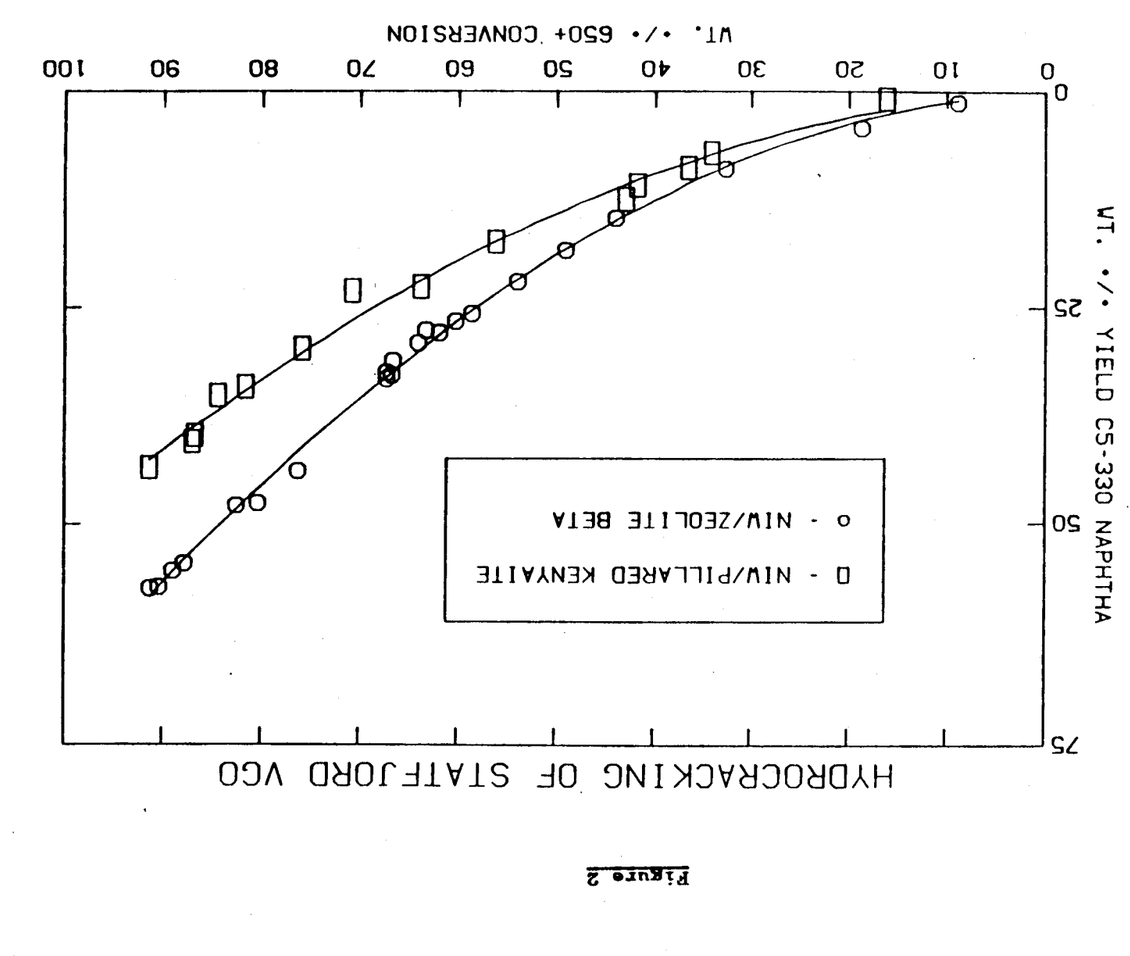
FIGS. 2 and 3 compare the $C_1$ to $C_4$ light gas and naphtha selectivities for NiW/pillared kenyaite and NiW/zeolite beta catalysts.
Figure 3:
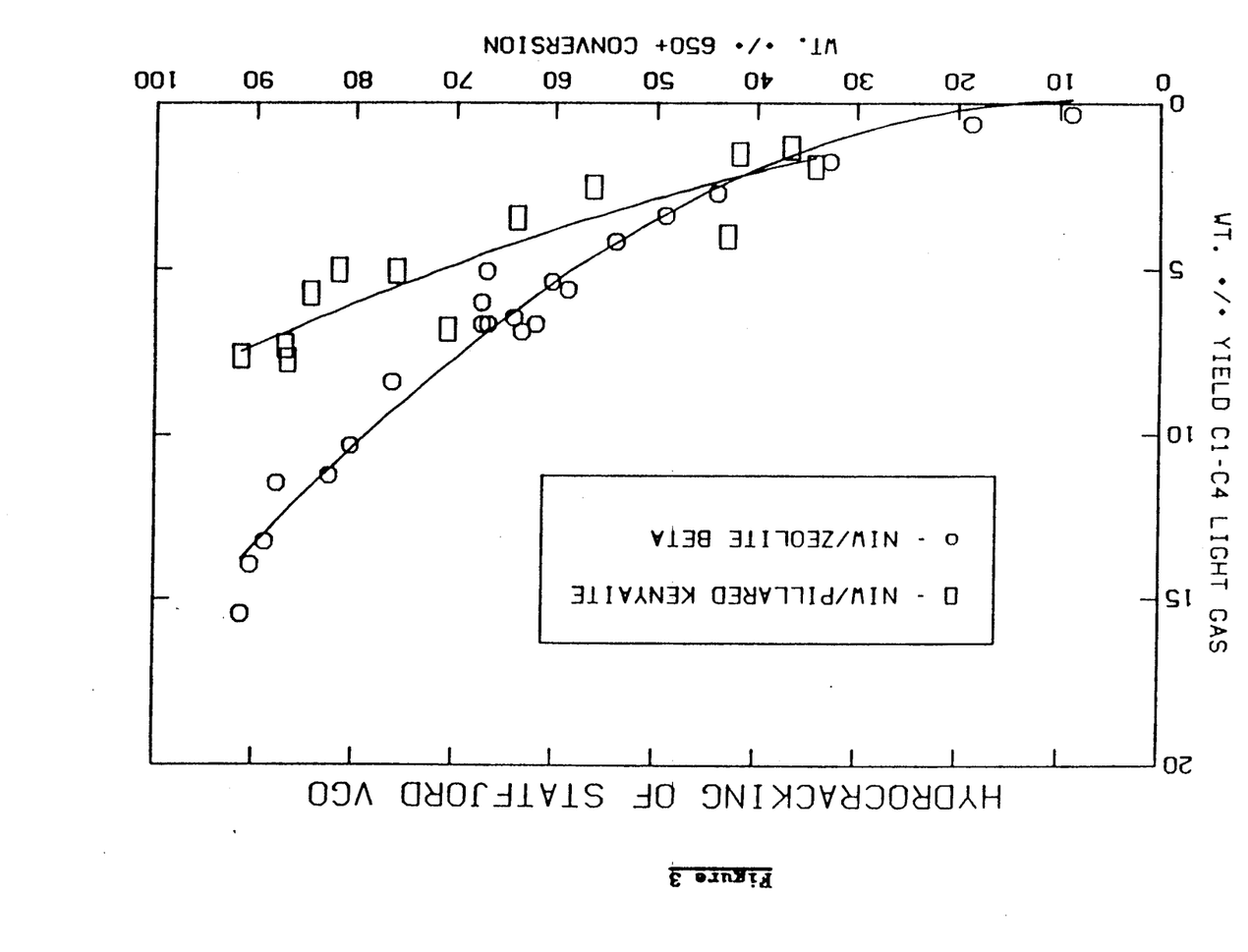

FIGS. 2 and 3 compare the $C_1$ to $C_4$ light gas and naphtha selectivities for the NiW/pillared kenyaite and NiW/zeolite beta catalysts. The comparatively low selectivity for light gas production is an additional highly desirable feature of the kenyaite catalyst. Table 4 compares the product yield structures from the NiW/zeolite beta and the NiW/pillared kenyaite catalysts at about 83 wt % conversion.

TABLE 4

| | NiW/Zeolite Beta | NiW/Pillared Kenyaite |
|---|---|---|
| Temperature, °F. | 721 | 766 |
| Pressure, psig | 1450 | 1450 |
| LHSV, $hr^{-1}$ | 0.52 | 0.22 |
| WHSV, $hr^{-1}$ | 0.75 | 0.39 |
| $H_2$ flow, scf/BBL | 4600 | 6100 |
| Conversion, wt % | 83 | 82 |
| Yields, wt % | | |
| 330–650° F. dist. | 23 | 42 |
| $C_5$–330° F. naph. | 48 | 34 |
| $C_1$–$C_4$ Gas | 11 | 5 |

What is claimed is:

1. A process comprising hydrocracking a hydrocarbon feedstock having an initial boiling point about 343° C. in the presence of a catalyst having cracking and hydrogenating activity, said catalyst comprising a layered silicate containing interspathic polymeric silica, in order to produce a hydrocarbon product having at least 35 percent by weight of hydrocarbons having a boiling point below 343° C., said catalyst further comprising at least one metal selected from the group consisting of Cr, Mo, W, Fe, Co, and Ni, wherein said hydrocracking occurs at conversions to product having a boiling point of less than 343° C. of greater than 70 percent volume of charge.

2. A process according to claim 1, wherein said layered silicate further contains an interspathic polymeric oxide of an element selected from the group consisting of Al, B, Cr, Ga, In, Mo, Nb, Ni, Ti, Tl, W, and Zr.

3. A process according to claim 1, wherein said layered silicate further contains an interspathic polymeric oxide of Al.

4. A process according to claim 1, wherein said hydrocracking occurs at temperatures ranging from about 250° C. to about 500° C., hydrogen pressures ranging from about 2 to about 21 MPa, liquid hourly space velocites ranging from about 0.05 to about 10 and $H_2$ circulations ranging from about 500 to about 10,000 scfb.

5. A process according to claim 1, wherein said hydrocracking occurs at conversions to product having a boiling point of less than 343° C. of greater than 75 percent volume of charge.

6. A process according to claim 3, wherein said catalyst further comprises W and Ni.

7. The process according to claim 1, wherein said hydrocarbon feedstock is hydrotreated prior to said hydrocracking.

8. A process according to claim 1, wherein said layered silicate comprising interspathic polymeric silica has an interlayer distance greater than about 10 angstroms.

9. A process according to claim 8, wherein said interlayer distance is greater than about 15 angstroms.

10. A process according to claim 6, wherein said layered silicate contains an interspathic polymeric oxide of aluminum.

11. A process according to claim 6, wherein said catalyst contains about 0.1 to 20 weight percent of at least one element selected from the group consisting of W and Ni.

12. A process according to claim 1, wherein said layered silicate is selected from the group consisting of magadiite, natrosilite, kenyaite, makatite, nekoite, kanemite, okenite, dehayelite, macdonaldite and rhodesite.

13. A process according to claim 1, wherein said layered silicate is magadiite.

14. A process comprising hydrocracking a hydrocarbon feedstock having an initial boiling point above 343° C., hydrocracking taking place in the presence of a catalyst having cracking and hydrogenating activity, said catalyst comprising kenyaite containing interspathic polymeric silica and interspathic polymeric alumina, said catalyst further comprising Ni and W, said hydrocracking taking place under conditions to produce a hydrocarbon product having at least 70 percent by weight of hydrocarbons having a boiling point below 343° C., and at least 30 percent by weight of hydrocarbons having a boiling point between 165° C. and 343° C.

* * * * *